United States Patent
Govari

(10) Patent No.: US 10,828,008 B2
(45) Date of Patent: Nov. 10, 2020

(54) STEAM POP DETECTION

(71) Applicant: Biosense Webster (Israel) LTD., Yokneam (IL)

(72) Inventor: Assaf Govari, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 510 days.

(21) Appl. No.: 15/457,708

(22) Filed: Mar. 13, 2017

(65) Prior Publication Data
US 2018/0256129 A1 Sep. 13, 2018

(51) Int. Cl.
A61B 18/14 (2006.01)
A61B 7/02 (2006.01)
(Continued)

(52) U.S. Cl.
CPC .............. *A61B 7/023* (2013.01); *A61B 5/061* (2013.01); *A61B 18/1492* (2013.01); *A61B 34/20* (2016.02); *A61B 5/6887* (2013.01); *A61B 5/7267* (2013.01); *A61B 7/026* (2013.01); *A61B 7/04* (2013.01); *A61B 2017/0011* (2013.01);
(Continued)

(58) Field of Classification Search
CPC ................. A61B 34/20; A61B 5/6805; A61B 2035/2063
See application file for complete search history.

(56) References Cited

U.S. PATENT DOCUMENTS 5,733,281 A * 3/1998 Nardella ............ A61B 18/1206 606/38
7,037,268 B1 5/2006 Sleva et al.
(Continued)

FOREIGN PATENT DOCUMENTS

EP 3090697 A1 11/2016
WO 00/54897 A2 9/2000
WO 2013101321 A1 7/2013

OTHER PUBLICATIONS

Chik, W.W.B., et al., "Acoustic Signal Emission Monitoring as a Novel Method to Predict Steam Pops During Radiofrequency Ablation: Preliminary Observations," Journal of Cardiovascular Electrophysiology, Apr. 2015, vol. 26 (4), 8 pages.
(Continued)

*Primary Examiner* — Michael F Peffley
*Assistant Examiner* — Bo Ouyang
(74) *Attorney, Agent, or Firm* — Etan S. Chatlynne; Roberts Calderon Safran & Cole P.C.

(57) ABSTRACT

Medical apparatus includes an elongate probe for insertion into a body of a patient. The probe includes an ablation element and an acoustic transducer disposed at a distal end of the probe. An array of acoustic sensors is placed over the body. While the distal end of the probe is positioned in a target location in the body, a control unit drives the acoustic transducer in a training phase to emit an acoustic signal, receives electrical signals from the acoustic sensors in response to the acoustical signal, and processes the electrical signals so as to derive a phase profile focused at the target location. In an operational phase, the control unit drives the ablation element to ablate tissue in the body at the target location, and receives and filters the electrical signals from the acoustic sensors using the phase profile so as to detect acoustical activity at the target location.

14 Claims, 2 Drawing Sheets

(51) Int. Cl.
    *A61B 34/20*     (2016.01)
    *A61B 5/06*     (2006.01)
    *A61B 5/00*     (2006.01)
    *A61B 7/04*     (2006.01)
    *A61B 18/00*     (2006.01)
    *A61B 17/00*     (2006.01)

(52) U.S. Cl.
    CPC ............... *A61B 2018/00357* (2013.01); *A61B 2018/00577* (2013.01); *A61B 2018/00642* (2013.01); *A61B 2034/2063* (2016.02); *A61B 2562/0204* (2013.01)

(56) References Cited

U.S. PATENT DOCUMENTS

| | | | |
|---|---|---|---|
| 8,545,409 B2 | 10/2013 | Sliwa et al. | |
| 2001/0039419 A1 | 11/2001 | Francischelli et al. | |
| 2003/0204184 A1 | 10/2003 | Ferek-Patric | |
| 2005/0090725 A1 | 4/2005 | Page et al. | |
| 2011/0288605 A1* | 11/2011 | Kaib | A61B 5/0006 607/5 |
| 2012/0123243 A1* | 5/2012 | Hastings | A61B 8/0841 600/411 |
| 2016/0324569 A1* | 11/2016 | Hoitink | A61B 18/1492 |

OTHER PUBLICATIONS

European Search Report for European Application No. 18161146, dated Jul. 26, 2018, 7 pages.

* cited by examiner

STEAM POP DETECTION

FIELD OF THE INVENTION

The present invention relates generally to medical devices and systems, and specifically to monitoring of invasive medical procedures.

BACKGROUND

Catheter-based ablation of myocardial tissue is commonly used in treating cardiac arrhythmias. Such treatment typically involves applying radio-frequency (RF) electrical energy to ablate the tissue and thus block undesired activation currents. It is critical that the physician apply RF energy of sufficient intensity to create ablation lesions of the required depth to entirely block the undesired currents. Too much RF energy, however, is liable to cause excessive tissue damage and even puncture the heart wall, with life-threatening consequences.

Excessive ablation energy frequently gives rise to cavitation, as fluids in the tissue vaporize with explosive force. This phenomenon is commonly referred to as a "steam pop." Typically, as the energy is applied at a given location, steam pops will begin on a small scale and will then escalate (often very quickly) to explosions strong enough to be audible outside the body. By the time the steam pops reach this level, however, it may be too late to turn down the ablation energy and prevent serious tissue damage.

Various techniques have been proposed for sensing of acoustical activity associated with ablation. For example, U.S. Patent Application Publication 2001/0039419 describes an ablation apparatus that includes a maneuvering mechanism, a conductive element attached to the apparatus, a sensor attached to the apparatus and an output device in communication with the sensor. The sensor senses vibration during the ablation procedure and sends a signal to the output device to reduce power to the conductive element.

As another example, U.S. Pat. No. 5,733,281 describes an electrosurgical feedback system for detecting the effects of electrosurgical energy on tissue. The feedback system can include an acoustical detection element that acoustically detects the effects of energy on tissue and then generates an acoustic output signal indicative of these energy effects. A power regulation element, in response to the acoustic output signal, regulates the electrosurgical energy supplied to the tissue.

SUMMARY

Embodiments of the present invention that are described hereinbelow provide improved methods and systems for monitoring ablation procedures in the body of a patient.

There is therefore provided, in accordance with an embodiment of the invention, medical apparatus, including an elongate probe configured for insertion into a body of a patient. The probe includes an ablation element and an acoustic transducer disposed at a distal end of the probe. An array of acoustic sensors is configured to be placed over the body of the patient. A control unit is configured, while the distal end of the probe is positioned in a target location in the body, to drive the acoustic transducer in a training phase to emit an acoustic signal, to receive electrical signals from the acoustic sensors in response to the acoustical signal, and to process the electrical signals so as to derive a phase profile focused at the target location. The control unit is further configured, in an operational phase, to drive the ablation element to ablate tissue in the body at the target location, and to receive and filter the electrical signals from the acoustic sensors using the phase profile so as to detect acoustical activity at the target location.

In a disclosed embodiment, the acoustic sensors are mounted on a vest, which is configured to be placed over a thorax of the patient.

In some embodiments, the acoustic sensors include microphones. Additionally or alternatively, the acoustic transducer includes a piezoelectric crystal, and the control unit is configured to drive the piezoelectric crystal with electrical pulses.

In some embodiments, the ablation element includes an electrode, and the control unit is configured to drive the electrode with radio frequency (RF) electrical energy, and the probe includes a catheter, which is configured for insertion into a chamber of a heart of the patient, so as to ablate myocardial tissue at the target location. In a disclosed embodiment, the control unit is configured to process the filtered electrical signals so as to detect steam pops occurring at the target location.

There is also provided, in accordance with an embodiment of the invention, a method for monitoring treatment, which includes inserting an elongate probe into a body of a patient, with an ablation element and an acoustic transducer disposed at a distal end of the probe. An array of acoustic sensors is placed over the body of the patient. In a training phase, while the distal end of the probe is positioned in a target location in the body, the acoustic transducer is driven to emit an acoustic signal, and electrical signals are received from the acoustic sensors in response to the acoustical signal and are processed so as to derive a phase profile focused at the target location. In an operational phase, while the distal end of the probe is positioned in the target location, the ablation element is driven to ablate tissue in the body at the target location, and the electrical signals from the acoustic sensors are received and filtered using the phase profile so as to detect acoustical activity at the target location.

The present invention will be more fully understood from the following detailed description of the embodiments thereof, taken together with the drawings in which:

DETAILED DESCRIPTION OF EMBODIMENTS

Figure 1:
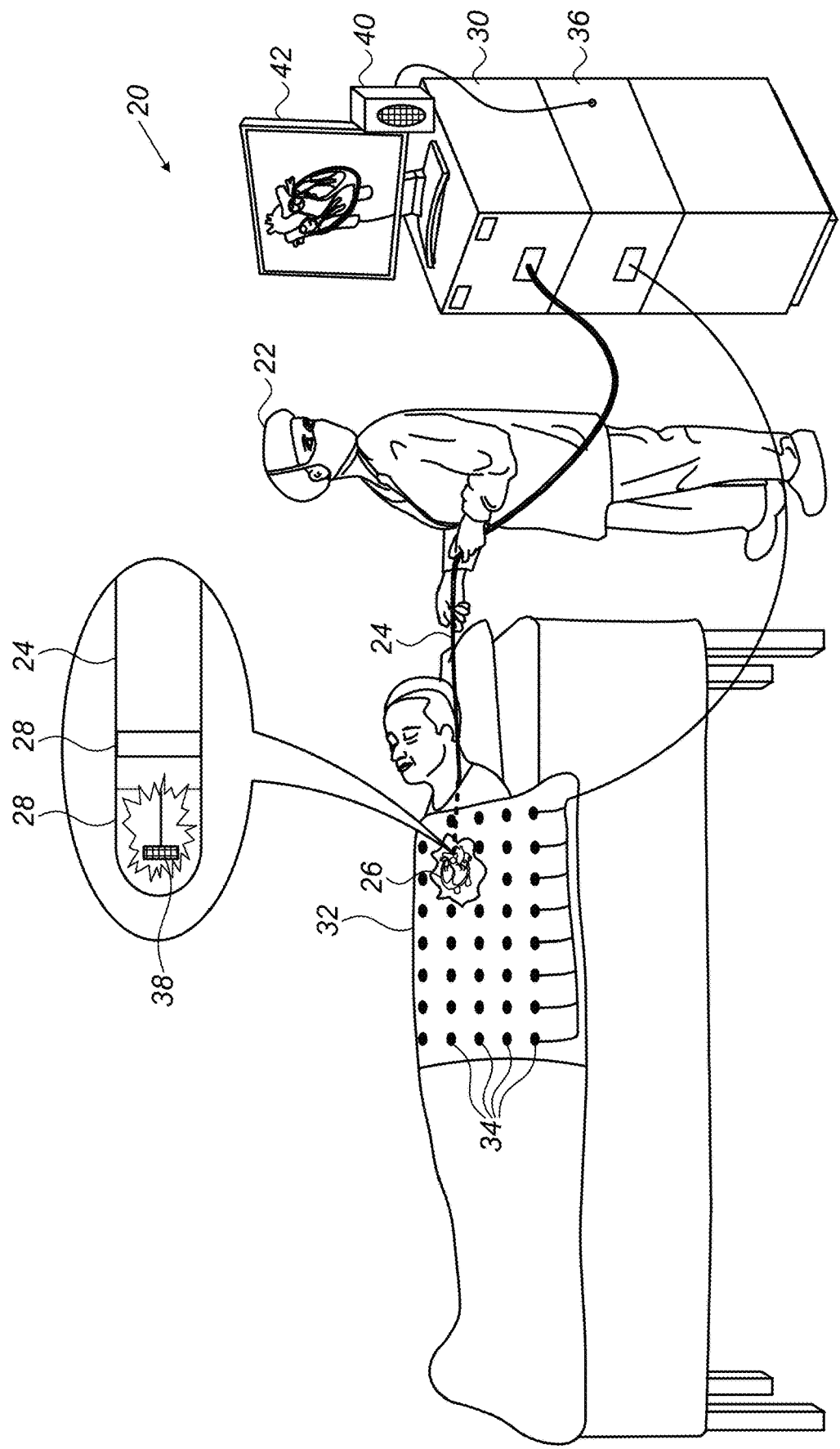
FIG. 1 is a schematic pictorial illustration of a system for intracardiac ablation and monitoring, in accordance with an embodiment of the invention.

Early detection of steam pops, when they are just beginning to occur during an ablation procedure, can be a valuable tool in avoiding serious tissue damage. Existing detection techniques, however, lack the sensitivity to detect steam pops at this early stage, when the faint sound of small steam pops may be masked by background sounds. By the time the steam pops become clearly audible, the damage to tissue may already have been done.

Embodiments of the present invention that are described herein address this difficulty by enabling more sensitive, focused detection of sounds emitted from the ablation site. These embodiments use an array of acoustic sensors placed over the body of the patient as a phased array. The phases in the array are tuned so as to focus on sounds originating from the location of the ablation, while effectively canceling out sounds originating from surrounding regions. The array thus acts as a highly directional microphone, which allows steam pops at the ablation location—even very faint steam pops—to be detected, by automatic signal processing and/or human staff on hand, with high sensitivity.

In the disclosed embodiments, an elongate probe, such as a catheter, is inserted into a body of a patient. The probe comprises an ablation element, such as an electrode, and an acoustic transducer, such as a piezoelectric crystal, both of which are disposed at the distal end of the probe. An array of acoustic sensors, such as an array of miniature microphones mounted on a suitable vest, is placed over the body of the patient, surrounding a target location in the body at which the probe is to perform an ablation procedure.

Once the distal end of the probe has been positioned at the target location, a control unit operates the probe and sensor array in two successive phases: In a training phase, the control unit drives the piezoelectric transducer to emit an acoustic signal and receives electrical signals from the acoustic sensors in response to this acoustical signal. The control unit processes these electrical signals so as to derive a phase profile that is effectively focused at the target location. Next, in an operational phase, the control unit drives the ablation element to ablate tissue in the body at the target location, while continuing to receive the electrical signals from the acoustic sensors. The control unit filters these signals using the phase profile derived in the training phase, and is thus able to detect acoustical activity at the target location with enhanced sensitivity while rejecting background sounds.

Although the disclosed embodiments refer specifically to radio frequency (RF) electrical ablation of myocardial tissue, the techniques that are described herein for trained, phased-array acoustic detection at locations in the body may alternatively be applied using other sorts of probes, ablation elements, acoustic transducers and sensors, in monitoring various sorts of medical procedures. All such alternative implementations are considered to be within the scope of the present invention.

FIG. 1 is a schematic pictorial illustration of a system 20 for intracardiac ablation and monitoring, in accordance with an embodiment of the invention. An operator 22, typically a physician, inserts a catheter 24 through the vascular system of a patient into a chamber of the patient's heart 26. As shown in the inset in FIG. 1, one or more electrodes 28 are disposed over the distal end of catheter 24. Once operator 22 has navigated the distal tip of catheter 24 to a target location in heart 26, a control unit 30 drives electrodes 28 with RF electrical energy to ablate tissue at the location. For this purpose, control unit 30 typically comprises an RF frequency generator and high-power amplifiers, which drive the RF electrical energy through conductors (not shown) in catheter 24, along with suitable frequency and power control circuits, as are known in the art.

Navigation of catheter 24 may be facilitated by techniques that are known in the art, such as magnetic or electrical position sensing, and/or image-based tracking. For example, suitable magnetic and electrical position sensing capabilities are offered by the CARTO system, produced by Biosense Webster Inc. (Diamond Bar, Calif.). These aspects of the operation of system 20, however, are beyond the scope of the present disclosure.

To enable detection of faint steam pops that may be caused by the ablation of tissue in system 20, a vest 32 comprising an array of small microphones 34 is placed over the patient's thorax. The term "vest" in this context refers to a flexible covering, made from a fabric or other suitable material, that fits securely around the thorax so that microphones 34 are held stably in place against the thorax. Microphones 34 may comprise any suitable sort of acoustical sensors, such as omnidirectional piezoelectric elements, which output electrical signals in response to acoustical vibrations.

A phase-sensitive acoustic processor 36 in control unit 30 receives and processes the electrical signals that are output by microphones 34. In processing these signals, processor 36 applies a phase profile that is selected so as to focus acoustic reception on the location of the distal end of catheter 24. This profile is computed and updated dynamically as catheter 24 moves from location to location in heart 26. To enable processor 36 to compute the phase profile accurately, catheter 24 comprises an acoustic transducer 38, such as a miniature piezoelectric element (also referred to as an audio transducer), in its distal end. The use of transducer 38 and microphones 34 in computing the phase profile is described hereinbelow with reference to FIG. 2.

During the ablation procedure, processor 36 applies the appropriate phase profile in filtering the electrical signals output by microphones 34 so as to generate an output in which sounds originating from the current location of the distal end of catheter 24 are amplified, while background sounds are suppressed. Processor 36 may play this output in analog audio form, via a speaker 40, for example, so that operator 22 can hear and respond to the sounds (particularly faint, early-stage steam pops). Additionally or alternatively, processor 36 may apply digital audio recognition to the output in order to recognize steam pops, for example by frequency-domain matching to a steam pop template. In this latter case, processor 36 may, upon detecting suspected steam pops, automatically reduce or shut off the RF ablation energy. Additionally or alternatively, processor 36 may drive a display 42 or other user output device to warn operator 22 of the possible occurrence of steam pops.

Processor 36 typically comprises a suitable general-purpose computer processor, along with front-end circuits for amplifying and filtering the signals from microphones and converting the signals to digital form for processing. The processor is programmed in software to carry out the functions described herein and may also be used in performing other functions of control unit 30. Alternatively or additionally, processor 36 may comprise one or programmable digital signal processors, which are programmed to carry out these processing functions. Further alternatively or additionally, at least some of the functions of processor 36 may be carried out by hard-wired digital logic or analog processing circuits. All such alternative implementations are considered to be within the scope of the present invention.

Figure 2:
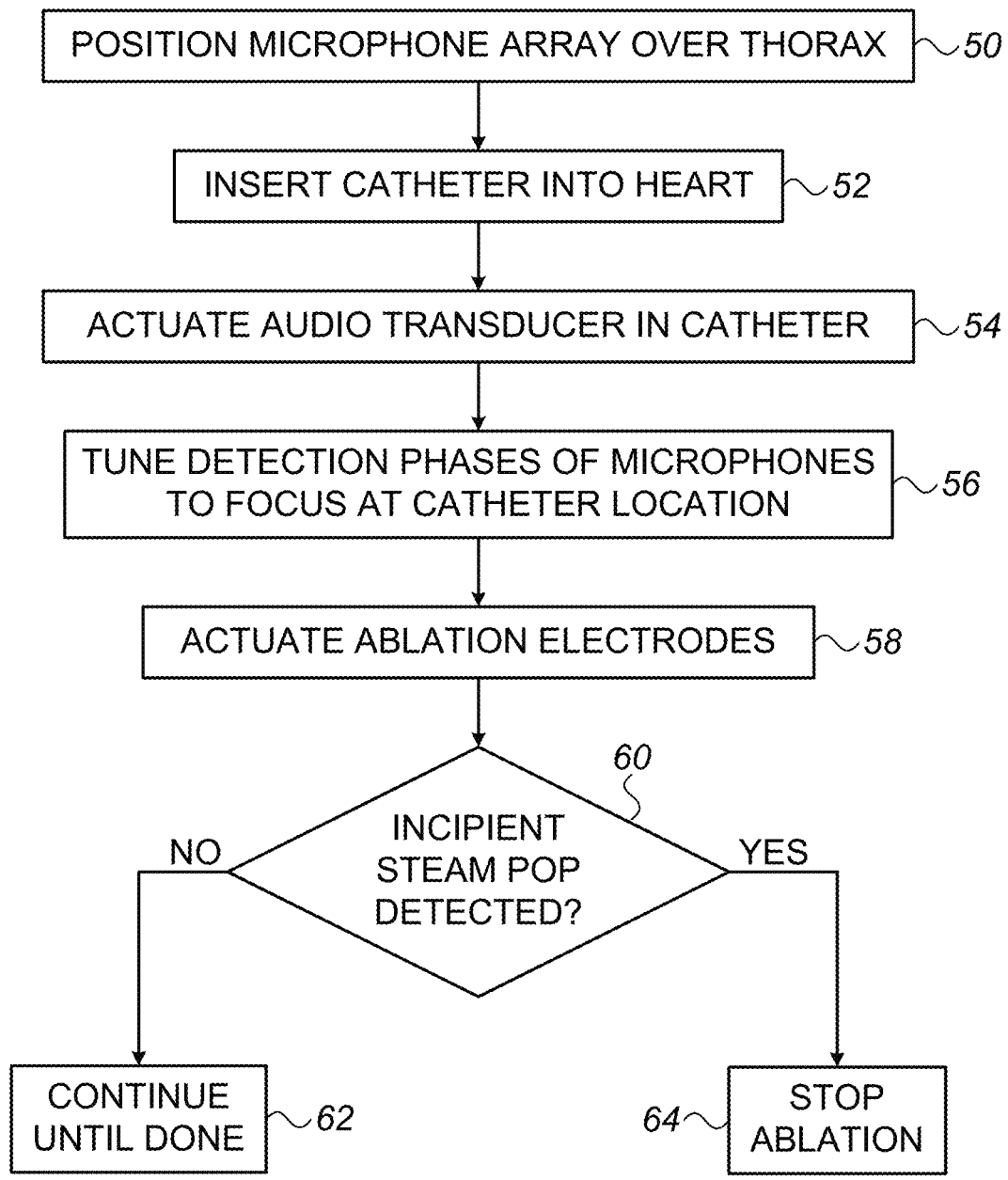
FIG. 2 is a flow chart that schematically illustrates a method for monitoring an ablation procedure, in accordance with an embodiment of the invention.

FIG. 2 is a flow chart that schematically illustrates a method for monitoring an ablation procedure, in accordance with an embodiment of the invention. The method is described, for the sake of concreteness and clarity, with reference to the elements of system 20 that are shown in FIG. 1, but the principles of this method may alternatively be implemented in other system configurations, for monitoring this and other sorts of ablation procedures.

As an initial step in operation of system 20, vest 32 containing the array of microphones 34 is positioned securely over the patient's thorax, at an array positioning step 50. Operator 22 then inserts catheter into heart 26 and positions the distal end of the catheter at a target location, where ablation is to be carried out, at a catheter insertion step 52.

Processor 36 now initiates a training phase, by driving acoustic transducer 38 to emit an acoustic signal, at an audio actuation step 54. Processor 36 receives the electrical signals that are output by microphones 34 in response to this acoustical signal, and processes these signals so as to derive a phase profile focused at the target location, at a detection tuning step 56. The phase profile typically comprises a respective phase delay in the signal output by each microphone 34. In other words, if transducer 38 is driven at step 54 to emit short audio pulses, the respective phase delay of each microphone can be represented simply by the time it takes for the corresponding pulse to appear in the electrical signal output by the microphone, relative to a predefined reference. Alternatively, frequency-domain analysis may be applied in order to derive a more complex, spectral phase profile.

The phase profile determined at steps 54 and 56 is local, i.e., it applies to the specific location in heart 26 wherein the distal end of catheter 24 is currently positioned. Although the same phase profile may be used at a number of locations in mutual proximity (for example, when a line of ablation lesions is to be formed), it may be desirable to repeat the training phase when the catheter is shifted to a new location.

Once the phase profile has been determined in the training phase, control unit 30 initiates the operational phase, driving electrode (or electrodes) 28 to ablate tissue in heart 26 at the target location, at an ablation step 58. Processor 36 receives and filters the electrical signals from microphones 34 using the phase profile so as to detect acoustical activity specifically at the ablation location, at an acoustical detection step 60. Processor 36 thus operates the array of microphones as a phased array, by applying the appropriate, respective phase adjustment (advance or delay) to the signal from each microphone, and then summing the phase-adjusted signals. In the simple example given above, in which the phase delay is measured for each microphone in response to an audio pulse emitted by transducer 38, processor 36 can achieve the desired phased-array performance by applying the inverse of the measured delay to the signal from each microphone. (In other words, if the pulse from a given microphone was received X milliseconds before the reference time, processor 36 will apply a delay of X milliseconds to the signal from this microphone, and vice versa.)

Based on the filtered, summed signal found at step 60, either operator 22 or processor 36 (or both) decides whether any steam pops are audible. If not, ablation continues until done, at an ablation completion step 62. If incipient steam pops are detected, however, ablation is stopped, at an ablation interruption step 64. This step may be carried out automatically by control unit 30 and/or manually by operator 22. Alternatively, if only very faint steam pops are heard, it may be possible to continue the ablation at reduced RF energy.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Medical apparatus, comprising:
    an elongate probe configured for insertion into a body of a patient, the probe comprising an ablation element and an acoustic transducer disposed at a distal end of the probe;
    an array of acoustic sensors configured to be placed over the body of the patient; and
    a control unit, which is configured, while the distal end of the probe is positioned in a target location in the body, to drive the acoustic transducer in a training phase to emit an acoustic signal, to receive electrical signals from the acoustic sensors in response to the acoustical signal, and to process the electrical signals so as to derive a phase profile focused at the target location, and which is further configured, in an operational phase, to drive the ablation element to ablate tissue in the body at the target location, and to receive and filter the electrical signals from the acoustic sensors using the phase profile so as to detect acoustical activity at the target location.

2. The apparatus according to claim 1, wherein the acoustic sensors are mounted on a vest, which is configured to be placed over a thorax of the patient.

3. The apparatus according to claim 1, wherein the acoustic sensors comprise microphones.

4. The apparatus according to claim 1, wherein the acoustic transducer comprises a piezoelectric crystal, and wherein the control unit is configured to drive the piezoelectric crystal with electrical pulses.

5. The apparatus according to claim 1, wherein the ablation element comprises an electrode, and wherein the control unit is configured to drive the electrode with radio frequency (RF) electrical energy.

6. The apparatus according to claim 1, wherein the control unit is configured to process the filtered electrical signals so as to detect steam pops occurring at the target location.

7. The apparatus according to claim 1, wherein the probe comprises a catheter, which is configured for insertion into a chamber of a heart of the patient, so as to ablate myocardial tissue at the target location.

8. A method for monitoring treatment, comprising:
    inserting an elongate probe into a body of a patient, the probe comprising an ablation element and an acoustic transducer disposed at a distal end of the probe;
    placing an array of acoustic sensors over the body of the patient;
    in a training phase, while the distal end of the probe is positioned in a target location in the body:
        driving the acoustic transducer to emit an acoustic signal;
        receiving electrical signals from the acoustic sensors in response to the acoustical signal; and
        processing the electrical signals so as to derive a phase profile focused at the target location; and
    in an operational phase, while the distal end of the probe is positioned in the target location:
        driving the ablation element to ablate tissue in the body at the target location; and
        receiving and filtering the electrical signals from the acoustic sensors using the phase profile so as to detect acoustical activity at the target location.

9. The method according to claim 8, wherein the acoustic sensors are mounted on a vest, which is placed over a thorax of the patient.

10. The method according to claim 8, wherein the acoustic sensors comprise microphones.

11. The method according to claim 8, wherein the acoustic transducer comprises a piezoelectric crystal, and wherein driving the acoustic transducer comprises applying electrical pulses to the piezoelectric crystal.

12. The method according to claim 8, wherein the ablation element comprises an electrode, and wherein driving the ablation element comprises applying radio frequency (RF) electrical energy to the electrode.

13. The method according to claim 8, and comprising processing the filtered electrical signals so as to detect steam pops occurring at the target location.

14. The method according to claim 8, wherein the probe comprises a catheter, which is configured for insertion into a chamber of a heart of the patient, so as to ablate myocardial tissue at the target location.

\* \* \* \* \*